United States Patent [19]

Jost

[11] Patent Number: 5,683,984
[45] Date of Patent: Nov. 4, 1997

US005683984A

[54] ENTERAL TUBE FEEDING COMPOSITION WITH A NATIVE MICELLAR CASEIN PROTEIN COMPONENT

[75] Inventor: Rolf Jost, La Tour-de-Peilz, Switzerland

[73] Assignee: Nestec S.A., Vevey, Switzerland

[21] Appl. No.: 380,344

[22] Filed: Jan. 30, 1995

[30] Foreign Application Priority Data

Feb. 25, 1994 [EP] European Pat. Off. ............ 94102851

[51] Int. Cl.$^6$ ............................ A61K 38/00; C07K 1/00; A23C 9/00

[52] U.S. Cl. ............... 514/21; 530/360; 530/361; 530/414; 530/832; 530/833; 424/157.1; 424/535; 426/491; 426/495; 426/580; 426/582; 426/587; 426/588

[58] Field of Search .................... 514/21; 530/360, 530/361, 414, 832, 833; 424/157.1, 535; 426/491, 495, 580, 582, 587, 588

[56] References Cited

U.S. PATENT DOCUMENTS

| | | | |
|---|---|---|---|
| 4,462,932 | 7/1984 | Lonergan | 260/119 |
| 4,485,040 | 11/1984 | Roger et al. | 260/122 |
| 5,143,741 | 9/1992 | Podolski et al. | 426/565 |
| 5,298,493 | 3/1994 | Mendy | 514/21 |
| 5,427,769 | 6/1995 | Berrocal et al. | 424/54 |
| 5,503,865 | 4/1996 | Behringer et al. | 426/587 |

FOREIGN PATENT DOCUMENTS

| | | |
|---|---|---|
| 0189160 | 7/1986 | European Pat. Off. . |
| 0527283 | 2/1993 | European Pat. Off. . |
| 3801391 | 7/1989 | Germany . |

OTHER PUBLICATIONS

Maubois, Australian Journal of Dairy Technology "New Applications of Membrane Technology in Dairy Industry" vol. 46, No. 2, Nov. 1991, pp. 91–95.

Krashenini, Derwent Abstract No. 88–18912 (1987)

Srilaorkul, et al., Journal of Dairy Science.

"Effect of Ultrafiltration of Skim Milk on Casein Micelle Size Distribution in Retentate" vol. 74, No. 1, Jan., 1991, pp. 50–57.

*Primary Examiner*—Cecilia J. Tsang
*Assistant Examiner*—Abdel A. Mohamed
*Attorney, Agent, or Firm*—Vogt & O'Donnell, LLP

[57] ABSTRACT

An enteral composition of protein, glucides, lipids and minerals, which is suitable for tube feeding, employs native micellar casein as the protein. The composition is prepared by obtaining native micellar casein and combining it with the glucides, lipids and minerals. A dispersion of micellar casein may be obtained by microfiltering milk, particularly skim milk, and glucides and minerals are dispersed in the micellar casein retentate obtained, lipids are added to the resulting dispersion and then the mixture is homogenized and sterilized. The microfiltered retentate may be diafiltered for obtaining the dispersion.

28 Claims, No Drawings

ENTERAL TUBE FEEDING COMPOSITION WITH A NATIVE MICELLAR CASEIN PROTEIN COMPONENT

BACKGROUND OF THE INVENTION

This invention relates to an enteral composition containing proteins, glucides and lipids.

An enteral composition is a sterilized liquid composition intended for feeding patients incapable of feeding themselves normally. It is administered by a nasal or oral tube leading directly to the digestive system and is supposed to supply three basic nutritive elements, namely proteins, glucides and lipids, in a suitable ratio and in a high calory density.

The choice of protein material for these enteral compositions is relatively limited. The majority of proteins are sensitive to heat and coagulate during sterilization. Caseinates are an exception and, accordingly, are widely used in this type of product, occasionally in association with soya proteins. The use of skimmed milk powder as a casein source is not an alternative to caseinates because it contains too much lactose which would lead to an enteral composition of laxative and hyperosmotic character.

Two types of caseinates are commonly used, namely sodium or potassium caseinate (Na/K caseinate) and calcium caseinate (Ca caseinate).

Na/K caseinate is soluble and has a high viscosity when its concentration exceeds 5%. This high viscosity is a major disadvantage for enteral and particularly nasal nutrition where particularly fine tubes are used. The enteral. Compositions require high concentrations of protein (5 to 10% by weight) to ensure that the calory input is accompanied by balanced protein/glucide/lipid ratios. The viscosity of Na/K caseinate limits its use to compositions containing less than 6 to 7% of protein.

Although not soluble, Ca caseinate forms a colloidal dispersion of relatively low viscosity in water. A major disadvantage of Ca caseinate is that it gives rise to the appearance of pronounced foreign tastes in the sterilized products.

SUMMARY OF THE INVENTION

The object of the present invention was to obviate the disadvantages described above by providing enteral compositions, as defined above, essentially containing native micellar casein as their protein source.

The native micellar casein replaces caseinates in enteral nutrition and is advantageous by virtue of enabling preparation of an enteral composition for tube feeding a patient which has a high protein concentration (5% to 10%) and a low viscosity and which has thermal stability to withstand sterilization.

The present invention also provides a process for preparing the enteral composition for tube feeding a patient comprising the nutritive elements of proteins, glucides and lipids wherein native micellar casein is obtained and employed as the protein for preparing the composition, the process being further characterized in that a milk, particularly skimmed milk, is microfiltered to isolate a retentate, which optionally is diafiltered, and then glucides and minerals are dispersed in the retentate, lipids are added to the resulting dispersion and the mixture is homogenized and then sterilized.

DETAILED DESCRIPTION OF THE INVENTION

The native micellar casein employed in accordance with the present invention is obtained from animal milk, such as cow's milk, goat's milk or ewe's milk. It is prepared by microfiltration of the milk.

The micellar protein is obtained by microfiltration of milk, optionally followed by diafiltration, on a membrane with a porosity of, for example, 0.1 to 0.2 micrometer.

EXAMPLES

Microfiltration selectively concentrates casein without retaining whey proteins, which is thus preferred for reasons of stability to sterilization.

Aside from its remarkable properties, the native micellar casein thus prepared has proved to be a protein source particularly suitable for enteral compositions. It does not have any of the disadvantages of the above-mentioned proteins:

its nutritional qualities are equivalent or superior to those of the proteins traditionally used, it forms a low-viscosity colloidal dispersion in water which enables it to be used in high concentrations (5 to 10%) without any flow problems in the finest tubes, it shows high thermal stability and thus withstands sterilization, for the same concentration, it gives solutions of lower osmolarity than caseinates, it has no taste whatever and it gives solutions with a whiteness superior to that of caseinates.

The invention is illustrated by the following Examples in which parts and percentages are by weight (g per 100 g of liquid composition) unless otherwise indicated.

Example 1

Preparation of Micellar Casein 300 kg of skimmed cow's milk, pasteurized for 15 s at 72° C., are treated in a microfiltration installation (TECHSEP® module 1S 151) equipped with 3.4 m² of membrane M 14 (mean pore diameter approximately 0.15 micrometer) at a temperature of 50° to 55° C. until 200 kg of permeate have been eliminated (which corresponds to concentration by a volume factor of 3). The retentate is then diafiltered with demineralized water by elimination of 500 kg of permeate (corresponding to a diafiltration volume factor of 5). The object of this diafiltration step is to produce the micellar casein with a protein purity of around 85% with less than 1% of residual lactose, based on total dry matter. The retentate is then concentrated to a final volume of 50 to 70 l which guarantees a dry matter content of 18 to 20%. The retentate contains 185 g/kg of total solids with a protein content of 84%, based on total dry matter. Its composition is as follows in g/kg of liquid:

Proteins 164
Lactose 0.4
Ash 15.6
Fats 1.3
Calcium 6
Potassium 0.1
Sodium 0.04
Phosphorus 1.7

Fractionation of the proteins in accordance with Rowland's scheme (Rowland, 1938; J. Dairy Res. 9, 42–46) shows that, since 96% of the total protein can be precipitated at pH 4.6, the retentate must be casein. Analysis of a dilute dispersion of retentate in a Malvern particle sizer shows that the casein is present in the form of particles with a mean diameter of 300 nanometers (nm) and that the distribution of the particles is relatively uniform (one family only ranging from 100 to 400 nm). This image corresponds exactly to that obtained for skimmed milk which indicates the presence of the micelles characteristic of milk.

Preparation of a Composition Intended for Enteral Nutrition 2.13 kg of the above retentate containing 19.5% total solids and corresponding to 350 g of proteins are transferred to a stirrer-equipped tank thermostatically controlled to 55° C. The following ingredients are then added to the dispersion in solid form (in g):
Maltodextrin MD-02 300
Sucrose 150
Tri-K citrate H$_2$O 20.33
MgCl$_2$ 6H$_{2O}$ 9.21
NaCl 5.84

After the ingredients have dissolved in the retentate, demineralized water is added to a total weight of 4825 g. At this stage, the pH is checked and, if necessary, adjusted to a value of 6.8. The fatty phase, i.e. 175 g of corn oil containing 2% (based on the oil) of soya lecithin as emulsifier, is then added. The mixture is homogenized in a two-stage homogenizer to 20 MPa in the first stage and then to 5 MPa in the second stage. The emulsion is then sterilized by indirect UHT treatment (heat exchanger) for 20 s at 130° C. or by direct UHT treatment (direct injection of steam) for 5 s at 148° C. or even by sterilization in cans or bags for 6 to 8 mins. at 120° C.

Three enteral compositions with the same energy density, i.e., 4.184 kJ/ml (1 kcal/ml) are thus prepared as described above:

| Proteins (% p/v) | Ingredient (%) | | |
|---|---|---|---|
| | Composition A 7 Native micellar casein | Composition B 7 Ca caseinate | Composition C 7 Na/K caseinate |
| Lipids (corn oil) | 3.5 | 3.5 | 3.5 |
| Glucides (maltodextrins/ sucrose) | 9.5 | 9.5 | 9.5 |
| Minerals Ca | 0.21 | 0.2 | 0.07 |
| K | 0.16 | 0.15 | 0.18 |
| Na | 0.05 | 0.05 | 0.06 |
| Mg | 0.03 | 0.03 | 0.02 |
| P | 0.12 | 0.12 | 0.07 |
| Cl | 0.1 | 0.1 | 0.03 |

The products obtained after sterilization in cans for 6 minutes at 120° C. are compared for their total protein content, their dynamic viscosity (shear rate 1600$^{s-1}$, ambient temperature), osmolarity and organoleptic properties:

| Composition | Proteins (total), % | Osmolarity mOsm/kgH$_2$O | Viscosity mPa · s | Presence of foreign tastes |
|---|---|---|---|---|
| A | 7.56 | 392 | 6 | No |
| B | 6.81 | 386 | 9 | Yes |
| C | 7.38 | 481 | 30 | Yes |

Composition A (native micellar casein) is clearly distinguished from composition C (Na/K caseinate) by its reduced viscosity and its low osmolarity. It is distinguished from composition B (Ca caseinate) by its viscosity and taste.

Example 2

An enteral composition with an energy density of 6.276 kJ/ml (1.5 kcal/ml) and 8% (p/v) of proteins is prepared from "low temperature" skimmed milk powder, i.e., skimmed milk dried under controlled thermal conditions.

20 kg of low-temperature skimmed milk powder are dispersed in 100 kg of demineralized water at a temperature of 50° to 55° C. This dispersion, which corresponds to twice-concentrated skimmed milk, is microfiltered in the same installation as in Example 1 in the diafiltration mode by passing demineralized water through until 600 kg of permeate have been eliminated. The retentate is then further concentrated to around 60 kg, which represents a dry matter content of 21% with a protein content, based on dry matter, of 82%.

To prepare the enteral composition, 2.323 kg of liquid retentate, representing 400 g of total proteins, are mixed at 55° C. with the following ingredients (g):
Maltodextrin MD-02 600
Sucrose 200
Tri-K citrate H$_2$O 20.33
MgCl$_2$6H$_2$O 9.21
NaCl 5.84

After the ingredients have dissolved in the retentate, demineralized water is added to a total weight of the dispersion of 4.7 kg. The pH is then adjusted to 6.8, after which 300 g of fatty phase are introduced, the total weight of the dispersion being 5 kg. After homogenization and sterilization as in Example 1, the product has a dynamic viscosity of 112 mPa.s (shear rate 1600$^{s-1}$, ambient temperature) it is white in appearance, has an agreeable sugary taste and is free from foreign tastes.

I claim:

1. In a process for preparing an enteral composition suitable for tube feeding wherein minerals are added together with a protein material, glucides and lipids in a medium for preparing an enteral composition suitable for tube feeding and then the composition is sterilized, the improvement comprising obtaining native micellar casein and employing the native micellar casein as the protein material for preparing the enteral composition.

2. A process according to claim 1 wherein milk is microfiltered for obtaining the micellar casein.

3. A process according to claim 2 wherein the milk is skim milk.

4. A process according to claim 1 wherein milk is microfiltered to obtain a retentate and the retentate is diafiltered for obtaining the micellar casein.

5. A process according to claim 4 wherein the milk is microfiltered and the retentate is diafiltered so that the retentate contains less than 1% by weight lactose.

6. A process according to claim 1 wherein milk is microfiltered to obtain a retentate and the retentate is diafiltered and concentrated to a dry matter content of from 18% to 20% for obtaining the micellar casein.

7. A process according to claim 6 wherein the milk is microfiltered and the retentate is diafiltered so that the retentate contains less than 1% by weight lactose.

8. A process according to claim 7 wherein the milk is skim milk.

9. The enteral composition of the process of claim 1.

10. The enteral composition of claim 9 wherein the composition contains the native micellar casein in an amount of from 5% to 10% by weight.

11. The enteral composition of claim 9 wherein the composition comprises protein which consists essentially of the native micellar casein.

12. A process for preparing an enteral composition suitable for tube feeding comprising obtaining a dispersion of native micellar casein, adding minerals and glucides to the micellar casein dispersion to obtain a dispersion supplemented with minerals and glucides and adding fat to the supplemented dispersion to obtain a composition suitable for enteral tube feeding, homogenizing the composition to obtain an emulsified composition and sterilizing the emulsified composition.

13. A process according to claim 12 wherein milk is microfiltered to obtain a retentate and the retentate is diafiltered and concentrated to a dry matter content of from 18% to 20% to obtain the micellar casein dispersion.

14. A process according to claim 12 wherein the milk is skim milk.

15. A process according to claim 12 further comprising prior to adding the fat to the supplemented dispersion, adjusting the pH of the supplemented dispersion to a value of 6.8.

16. A process according to claim 12 wherein milk is microfiltered to obtain the micecellar casein dispersion.

17. A process according to claim 16 wherein the milk is selected from the group consisting of cow milk, goat milk and ewe milk.

18. A process according to claim 12 wherein milk is microfiltered to obtain a retentate and then the retentate is diafiltered to obtain the micellar casein dispersion.

19. A process according to claim 18 wherein the milk is microfiltered and the retentate is diafiltered so that the micellar casein dispersion obtained contains less than 1% by weight lactose.

20. A process according to claim 19 wherein the milk is microfiltered and the retentate is diafiltered and concentrated so that the micellar casein dispersion contains less than 1% by weight lactose.

21. A process according to claim 20 wherein the milk is skim milk.

22. The enteral composition of the process of claim 12.

23. The enteral composition of claim 22 wherein the composition contains the native micellar casein in an amount of from 5% to 10% by weight.

24. The enteral composition of claim 22 wherein the composition comprises protein which consists essentially of the native micellar casein.

25. In an enteral composition which comprises protein, glucides, lipids and minerals and which is suitable for tube feeding, the improvement comprising that the protein consists essentially of native micellar casein.

26. An enteral composition according to claim 25 wherein the native micellar casein is an amount of from 5% to 10% by weight.

27. In a process for the tube feeding an enteral composition to a patient wherein the enteral composition comprises protein, glucides, lipids and minerals and is fed to the patient via a tube, the improvement comprising that the protein consists essentially of native micellar casein.

28. The process of claim 27 wherein the miceller casein is in an amount of from 5% to 10% by weight.

* * * * *